United States Patent [19]

Urata et al.

[11] Patent Number: 4,543,258

[45] Date of Patent: Sep. 24, 1985

[54] POLYOL ETHER COMPOUND, PREPARATION PROCESS THEREOF, AND COSMETIC COMPOSITION CONTAINING SAME

[75] Inventors: Koichi Urata; Naotake Takaishi; Yoshiaki Inamoto, all of Utsunomiya; Yuji Suzuki, Tokyo, all of Japan

[73] Assignee: Kao Corporation, Tokyo, Japan

[21] Appl. No.: 547,623

[22] Filed: Nov. 1, 1983

[30] Foreign Application Priority Data

Nov. 16, 1982 [JP] Japan ................................ 57-200587

[51] Int. Cl.$^4$ ............................................. A01N 25/00
[52] U.S. Cl. .................................... 514/772; 568/675; 568/679; 568/680; 514/938; 514/941
[58] Field of Search ...................... 568/675, 679, 680; 424/358, 365

[56] References Cited

FOREIGN PATENT DOCUMENTS 0071019 2/1983 European Pat. Off. ............ 568/679

*Primary Examiner*—Howard T. Mars

*Attorney, Agent, or Firm*—Oblon, Fisher, Spivak, McClelland & Maier

[57] ABSTRACT

Disclosed is a polyol ether compound represented by the general formula (I):

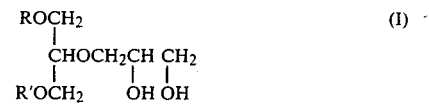

in which R represents a saturated or unsaturated, straight-chain or branched aliphatic hydrocarbon group having 8 to 24 carbon atoms, and R' represents a saturated or unsaturated, straight-chain or branched hydrocarbon group having 1 to 24 carbon atoms.

A preparation process of the compound (I) is also disclosed.

Compounds according to the invention show excellent emulsification stability and are suitable to be a cosmetic composition.

15 Claims, No Drawings

POLYOL ETHER COMPOUND, PREPARATION PROCESS THEREOF, AND COSMETIC COMPOSITION CONTAINING SAME

BACKGROUND OF THE INVENTION (i) Field of the Invention

This invention relates to 1,3-di-O-alkyl-2-O-2',3'-dihydroxypropyl glycerine compounds (which may be hereinafter referred to simply as position isomers of diglycerine dialkyl ethers) which are novel polyol ether compounds, processes for the preparation of the same, and cosmetic compositions comprising the compounds.

(ii) Description of the Prior Art

In the natural world, there are a number of polyhydric alcohol derivatives having ether bonds therein, typical of which are monoalkyl ethers of glycerine (hereinafter referred to as glyceryl ethers). For instance, lipids of fishes contain palmityl glyceryl ether (referred to as chimyl alcohol), stearyl glyceryl ether (batyl alcohol) and oleyl glyceryl ether (selachyl alcohol).

These glyceryl ethers have wide utility as a substrate for cosmetics because of their w/o type emulsifying characteristic (see Japanese Laid-open Application Nos. 87612/1974, 92239/1974 and 12109/1977, and Japanese Patent Publication No. 36260/1982). It is also known that the ethers have pharmacological actions such as erythropoietic stimulating effect to bone marrows, anti-inflammatory activity, and antitumor activity (see Japanese Patent Publication Nos. 10724/1974 and 18171/1977).

In view of the fact that the glyceryl ethers serve as unique surfactants which have a number of desirable characteristics, attempts have been made to derive polyol ether compounds, which have molecular structures similar to the glyceryl ethers (including ether bonds and hydrophilic OH groups in the molecule thereof), from polyhydric alcohols (see U.S. Pat. No. 2,258,892, Japanese Patent Publication No. 18170/1977, and Japanese Laid-open Application Nos. 137,905/1978 and 145,224/1979). The resulting polyol ether compounds show the w/o type emulsifying characteristics and are employed as a substrate for cosmetics (see West Germany OS No. 24 55 287) and also as an antimicrobial and fungicidal agent as well as an ordinary emulsifier.

The present inventors payed attention to such utility of polyol ether compounds and derived mono- and di-alkyl ethers of diglycerine, which ethers are polyol ether compounds, from alkyl glycidyl ethers which can readily be prepared from alcohols. Some patent applications have already been made on the application of such mono- and di-alkyl ethers of diglycerine as cosmetics substrates (Japanese Patent Application Nos. 81456/1981, 81457/1981 and 113404/1981).

SUMMARY OF THE INVENTION

We have made further studies and, as a result, found that novel polyol ether compounds of the general formula (I) have excellent surface active properties:

```
    ROCH2
     |
    CHOCH2CH CH2        (I)
     |       |   |
    R'OCH2   OH OH
``` in which R represents a saturated or unsaturated, straight-chain or branched aliphatic hydrocarbon group having 8 to 24 carbon atoms, and R' represents a saturated or unsaturated, straight-chain or branched hydrocarbon group having 1 to 24 carbon atoms.

Accordingly, an object of the present invention is to provide novel polyol ether compounds represented by the above formula (I).

Another object of the invention is to provide a process for preparing the compounds (I).

A further object of the invention is to provide cosmetics comprising the compounds (I).

DETAILED DESCRIPTION OF THE INVENTION AND PREFERRED EMBODIMENTS

The polyol ether compounds of the invention represented by the formula (I) are readily prepared in high yield and high purity from alkyl glycidyl ethers (II), which can be readily prepared from alcohols, by the following two processes (processes A and B).

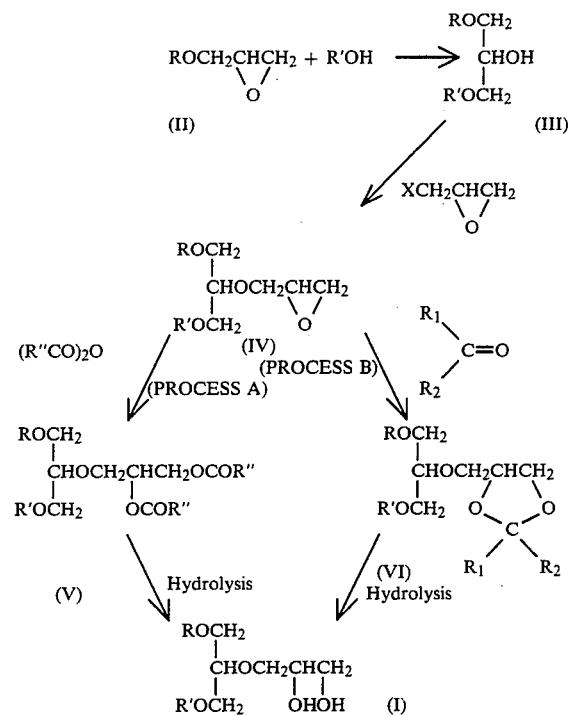

(in which $R_1$ represents hydrogen or a hydrocarbon group, $R_2$ represents a hydrocarbon group, R" represents a hydrocarbon group having 1 to 5 carbon atoms, X represents a halogen atom, and R and R' have the same meanings as defined above, respectively.)

Process A

An alcohol is added to the alkyl glycidyl ether (II) in the presence of an acid or base catalyst according to a known method (e.g. Germany OS No. 2535778), thereby forming 1,3-di-O-alkyl glycerine (III), followed by interacting an epihalohydrin and the 1,3-di-O-alkyl glycerine (III) according to Williamson's synthesis of ether to obtain an epoxide compound (IV). An acid anhydride is then added to the epoxide compound (IV) according to the method proposed by us (Japanese Patent Application No. 16061/1982) to obtain a diester compound (V). This diester compound (V) is hydrolyzed (saponified) to obtain an intended polyol ether compound (I).

Process B

To the epoxide compound (IV) obtained in the same manner as in the above process A is added a carbonyl compound according to the method proposed by us (Japanese Patent Application No. 133281/1981) to obtain a dioxolan compound (VI). The thus obtained dioxolan compound (VI) is hydrolyzed thereby obtaining an intended polyol ether compound (I).

In the above reactions, the 1,3-di-O-alkyl glycerine (III) which is an adduct of the alkyl glycidyl ether (II) and an alcohol has the reactive hydroxyl group at the 2 position. Alkylene oxides such as ethylene oxide, propylene oxide and the like are added to the reactive hydrogen whereby 1,3-di-O-alkyl-2-O-polyoxyalkylene glycerines which are nonionic active agents are obtained. The processes for preparing these compounds and applications thereof as an emulsifier have been already proposed such as in Japanese Laid-open Application No. 63936/1981, Germany OS Nos. 2139447 and 2139448, and the like. However, the polyol ether compounds of the present invention are completely different from the above compounds from the structural and preparatory aspects.

The reactions indicated above will now be described in detail.

The process A is first described. The alkyl glycidyl ether (II) used as one of starting materials in the process of the invention should have a saturated or unsaturated, straight-chain or branched aliphatic hydrocarbon group having from 8 to 24, preferably from 8 to 20 carbon atoms. Specific examples of the ether include: primary straight-chain alkyl glycidyl ethers such as n-octyl glycidyl ether, n-decyl glycidyl ether, n-dodecyl glycidyl ether, n-tetradecyl glycidyl ether, n-hexadecyl glycidyl ether, n-octadecyl glycidyl ether, n-octadecenyl glycidyl ether (oleyl glycidyl ether), docosyl glycidyl ether, and the like; primary branched alkyl glycidyl ethers such as 2-ethylhexyl glycidyl ether, 2-hexyldecyl glycidyl ether, 2-octyldodecyl glycidyl ether, 2-heptylundecyl glycidyl ether, 2-(1,3,3-trimethylbutyl)octyl glycidyl ether, 2-decyltetradecyl glycidyl ether, 2-dodecylhexadecyl glycidyl ether, 2-tetradecyloctadecyl glycidyl ether, 5,7,7-trimethyl-2-(1,3,3-trimethylbutyl)octyl glycidyl ether, methyl-branched isostearyl glycidyl ethers of the following formula:

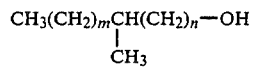

in which m is an integer of from 4 to 10, and n is an integer of from 5 to 11 provided that m+n=11 to 17 with a distribution having vertexes at m=7 and n=8; secondary alkyl glycidyl ethers such as sec-decyl glycidyl ether, sec-octyl glycidyl ether, sec-dodecyl glycidyl ether, and the like; and tertiary alkyl glycidyl ethers such as t-octyl glycidyl ehter, t-dodecyl glycidyl ether, and the like.

In recent years, there have been developed processes for preparing alkyl glycidyl ethers in high yield from alcohols (ROH) without isolation of halohydrin ethers (e.g. in Japanese Laid-open Application Nos. 141708/1979, 141709/1979, 141710/1979, 63974/1981, 108781/1981, and 115782/1981).

The alcohol (R'OH) which is added to the alkyl glycidyl ether (II) should have a saturated or unsaturated, straight-chain or branched hydrocarbon group having carbon atoms of from 1 to 24, preferably from 1 to 18 and most preferably from 1 to 10. Examples of the alcohol include: straight-chain aliphatic alcohols such as methyl alcohol, ethyl alcohol, propyl alcohol, butyl alcohol, octyl alcohol, decyl alcohol, hexadecyl alcohol, octadecyl alcohol, octadecenyl (oleyl) alcohol, and the like; branched aliphatic alcohols such as isopropyl alcohol, isobutyl alcohol, 2-ethylhexyl alcohol, 2-heptylundecyl alcohol, 5,7,7-trimethyl-2-(1,3,3-trimethylbutyl)octyl alcohol, and methyl-branched isostearyl alcohols represented by the following formula:

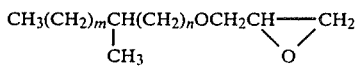

in which m is an integer of from 4 to 10, and n is an integer of from 5 to 11 provided that m+n=11 to 17 with a distribution having vertexes at m=7 and n=8; and alicyclic alcohols such as cyclohexyl alcohol, cyclopentyl alcohol, and the like.

The reaction at the first stage in which the alkyl glycidyl ether (II) and the alcohol are used to prepare 1,3-di-O-alkyl glycerine (III) is considered as an addition reaction of the alcohol with the epoxide bond derived from the terminal olefin. This addition reaction proceeds in the presence of either an acid or an alkali accompanied by the cleavage of the epoxide bond. However, when an acid catalyst is used, there is the danger that the cleavage takes place in two ways at alpha and beta positions, so that the alcohol is added at the alpha and beta positions, thereby giving two adducts. On the other hand, with an alkali catalyst, selective cleavage of the epoxide bond occurs at the alpha position, thereby selectively producing a product in which the alcohol is added at the alpha position i.e. the alcohol is added at the end portion of the molecule (see, for example, "KOGYO KAGAKU ZASSHI" Vol. 68, No. 4, pp. 663–669 (1965)). In this sense, it is preferable to use an alkali catalyst for the purpose of the present invention. Examples of the alkali catalyst include alkali metals such as Li, Na, K and the like, alkali metal hydroxides such as LiOH, NaOH, KOH and the like, and alkali metal alcoholates such as NaOMe, NaOEt, KOtBu and the like, tertiary amines such as triethylamine, tributylamine, tetramethylethylenediamine, tetramethyl-1,3-diaminopropane, tetramethyl-1,6-diaminohexane, pyridine, dimethylaniline, quinoline and the like.

The above reaction is effected by reacting the alkyl glycidyl ether (II) and 1 to 10 moles, preferably 1 to 5 moles of an alcohol in the presence of 0.001–0.2 mole, preferably 0.01 to 0.1 mole of an alkali catalyst, each based on per mole of the ether (II), under conditions of 70° to 150° C., preferably 70° to 120° C.

The resulting 1,3-di-O-alkyl glycerine (III) is then reacted with an epihalohydrin which is prepared by Williamson's synthesis of ether, thereby obtaining an epoxide compound (IV). This etherification reaction is preferably effected in the presence of a catalytic amount of a quaternary ammonium salt. The quaternary ammonium salts used for these purposes are preferably ammonium salts because of ease in industrial availability. Specific examples of the quaternary ammonium salts include tetraalkylammonium salts such as, for example, tetrabutylammonium chloride, tetrabutylammonium hydrogensulfate, trioctylmethylammonium chloride, lauryltrimethylammonium chloride, stearyltrimethyltriammonium chloride, benzyltrimethylammonium chloride, and the like, a group of alkylammonium salts having a polyoxyalkylene group such as, for example, tetraoxyethylene stearyldimethylammonium chloride, bistetraoxyethylene stearylmethylammonium chloride, and the like, betaine compounds, crown ethers, amine oxide compounds, and ion-exchange resins. These quaternary onium salts may be used in catalytic amounts but it is convenient to use 0.005 to 0.5 mole per mole of the 1,3-di-O-alkyl glycerine (III).

The reaction is effected in the presence of the quaternary onium salt catalyst using 1 to 10 moles, preferably 3 to 6 moles, per mole of the 1,3-di-O-alkyl glycerine (III), of an alkaline substance in the form of an aqueous solution (having a concentration of 10 to 80%, preferably 30 to 60%) in a reaction solvent such as an inert hydrocarbon such as, for exaple, hexane, benzene, toluene, xylene or the like at a reaction temperature of 30° to 70° C., preferably 40° to 60° C. The alkaline substance includes, for example, sodium hydroxide, potassium hydroxide, lithium hydroxide or the like. Of these, sodium hydroxide is conveniently used from the industrial standpoint.

To the resulting epoxide compound (IV) is added an acid anhydride in the presence of an acid or base catalyst, thereby giving a diester compound (V), followed by hydrolysis (saponification) to obtain an intended polyol ether compound.

The acid anhydrides used in the present invention include ordinary acid anhydrides. From the industrial standpoint and in view of ease in availability and after-treatment, anhydrides of lower acids are preferred. Specific examples of the anhydride include acetic anhydride, propionic anhydride, butyric anhydride, isobutyric anhydride, valeric anhydride, isovaleric anhydride, and the like. Of these, acetic anhydride is particularly preferred.

Other type of acid anhydride which is inexpensively available and important as an industrial meterial includes an anhydride of dibasic acid. For instance, the dibasic acid anhydrides are phthalic anhydride, succinic anhydride, maleic anhydride and the like. However, when these dibasic acid anhydrides are added to the glycidyl ether at 1,2 positions within the molecule thereof, the resulting adducts become unstable because they have such a highly-distorted structure as of the eight-membered ring and are thus unstable. In this connection, there is the possibility that the addition reaction takes place intermolecularly rather than the case where the eight-membered structure added at 1,2 positions within the molecule is formed, thereby causing the reaction to proceed so as to give a so-called polyester structure. From this, it is considered difficult to apply the dibasic acid anhydrides to the process of the present invention.

The acid catalysts used for the preparation of the diester compound (V) are conveniently Lewis acids. Examples of the Lewis acid include boron trifluoride ether complex, boron trifluoride acetate complex, boron trifluoride phenol complex, aluminum chloride, aluminum bromide, zinc chloride, tin tetrachloride, antimony chloride, titanium tetrachloride, silicon tetrachloride, ferric chloride, ferric bromide, cobalt(III) chloride, cobalt(III) bromide, and the like. The base catalysts are preferably tertiary amines. Examples of the tertiary amine include triethylamine, tripropylamine, tributylamine, trioctylamine, tetramethylethylenediamine, tetramethyl-1,3-diaminopropane, tetramethyl-1,6-diaminohexane, pyridine, quinoline, dimethylaniline, and the like.

In order to prepare the diester compound (V) from the epoxide compound (IV), it is usual to react an epoxide compound (IV) with 1 to 30 moles of an acid anhydride per mole of the epoxide compound (IV) in the presence of 0.001 to 0.2 mole of a Lewis acid or tertiary amine catalyst per mole of the epoxide compound (IV) at a temperature of 0° to 70° C. for the Lewis acid and 100°–150° C. for the tertiary amine. The amount of the acid anhydride is theoretically sufficient to be equimolar with the epoxide compound (IV). However, the reaction smoothly proceeds with higher yield when the acid anhydride is used in excess. Thus, it is effective to use the acid anhydride in amounts ranging from 2 to 20 moles, preferably 8 to 16 moles, per mole of the epoxide compound (IV).

The reaction using Lewis acids is an exothermic reaction and thus it is effective to control the reaction temperature in the range below 60° C., preferably 20° to 40° C., by suitable means such as cooling upon addition of the epoxide compound (IV) to an acid anhydride coexisting with a Lewis acid. Higher reaction temperatures may cause side reactions by the Lewis acid, e.g. polymerization of the epoxide compound (IV) or ring cleavage of the ether bond, to occur. With epoxide compounds (IV) having unsaturated bonds, there may occur the isomerization of the unsaturated bonds and the Wagner-Meerwein transfer reaction in combination. Accordingly, the reaction temperature should be accurately controlled.

On the other hand, when tertiary amines are used as the catalyst, no generation of heat takes place as is experienced in the use of Lewis acids. It is rather necessary to keep the reaction temperature high by application of heat. Preferably, a mixture of a tertiary amine and an acid anhydride is maintained at a temperature of 100° to 150° C., preferably 100° to 120° C., to which an epoxide compound (IV) is dropwise added. In this procedure, there is recognized no generation of heat and hence, it is necessary to maintain the temperature, for example, by application of heat during the course of the dropping of the epoxide compound (IV).

The reaction proceeds in the absence of any reaction solvent and it is the most suitable to use an excess of an acid anhydride serving also as a solvent. However, in order to suppress occurrence of the side reactions and control the reaction temperature, solvents may be used, if necessary. The reaction solvents may be any compounds which do not give any adverse influence on the reaction. Hydrocarbon solvents are suitably used. Examples of the hydrocarbon include aliphatic hydrocarbons such as pentane, hexane, heptane, octane and the like, aromatic hydrocarbons such as benzene, toluene, xylene and the like, alicyclic hydrocarbons such as cycloheptane, cyclohexane and the like, and mixtures thereof.

When the above reaction is carried out under such conditions as indicated above, the diester compound (V) is ordinarily obtained in a yield as high as about over 90% and may be purified using a technique such as distillation.

The hydrolysis reaction of the diester compound (V) in the subsequent step may be performed any known techniques. It is preferable to heat the compound in an aqueous solution of an alkaline substance such as sodium hydroxide, potassium hydroxide, lithium hydroxide, calcium hydroxide, sodium carbonate, calcium carbonate or the like. The amount of the alkaline substance is not critical. It is general to use 2 moles or more, preferably 2 to 5 moles, of the substance per mole of the diester compound (V). The hydrolysis proceeds in the absence of any reaction solvent but it is convenient to use a water-soluble solvent including, for example, a lower alcohol such as methanol, ethanol, isopropanol or the like, or an ether such as tetrahydrofuran, dioxane or the like and to reflux the mixture at a temperature of 50° to 100° C.

Upon hydrolysis of the diester compound (V) under conditions as indicated above, the 1,3-di-O-alkyl-2-O-2′,3′-dihydroxypropyl glycerine (I) which is a final product of the invention is quantitatively obtained.

Next, the process B is described. In the process B, a carbonyl compound is added to the epoxide compound (IV) obtained in the process A in the presence of an acid catalyst to obtain a dioxolan compound, followed by hydrolysis of the dioxolan compound thereby obtaining an intended polyol ether compound. The carbonyl compounds used in the practice of the invention include ordinary ketones and aldehydes. Examples of the ketone include aliphatic ketones such as acetone, methyl ethyl ketone, diethyl ketone, methyl propyl ketone, dipropyl ketone, ethyl propyl ketone, methyl hexyl ketone and the like, alicyclic ketones such as cyclobutanone, cyclopentanone, cyclohexanone, cyclooctanone and the like, and aromatic ketones such as acetophenone, benzophenone and the like. Examples of the aldehyde include aliphatic aldehydes such as formaldehyde, acetoaldehyde, propionaldehyde, octylaldehyde and the like, alicyclic aldehydes such as cyclopentyl aldehyde, cyclohexyl aldehyde and the like, and aromatic aldehydes such as benzaldehyde, naphthyl aldehyde and the like. Because of the ease in aftertreatment, lower carbonyl compounds having a small number of carbon atoms are preferably used. Most preferably, compounds having 6 or less carbon atoms are used.

The acid catalyst used for preparing the dioxolan compound (VI) may be either proton-donative acids or Lewis acids. Examples of the proton-donative acid include sulfuric acid, hydrochloric acid, phosphoric acid and the like, and examples of the Lewis acid include boron trifluoride etherate complex, boron trifluoride acetate complex, aluminum chloride, aluminum bromide, zinc chloride, tin tetrachloride, antimony chloride, titanium tetrachloride, silicon tetrachloride, ferric chloride, ferric bromide, cobalt(III) chloride, cobalt(III) bromide, zirconium chloride, boron oxide, acidic active alumina, and the like.

In order to prepare the dioxolan compound (VI) from the epoxide compound (IV), it was found convenient to react the epoxide compound (IV) with 1 to 30 moles of a carbonyl compound, based on unit mole of the epoxide compound (IV), in the presence of an acid catalyst in an amount of 0.001 to 0.2 mole per mole of the epoxide compound (IV) at a temperature of 0° to 70° C. Although it is theoretically sufficient to use equimolar amounts of the carbonyl compound and the epoxide compound (IV), the reaction proceeds more smoothly in higher yields when the carbonyl compound is used in larger amounts. Accordingly, it is convenient to use the carbonyl compound in amounts 2 to 15 moles, preferably about 7 moles, per mole of the epoxide compound (IV). The acid is used in catalytic amounts, i.e. in an amount of 0.001 to 0.3 mole, preferably 0.01 to 0.1 mole, per mole of the epoxide compound. Because this reaction is an exothermic reaction, the epoxide compound (IV) is added to a carbonyl compound coexisting with an acid catalyst during which a suitable operation such as cooling is applied to the reaction mixture thereby controlling the temperature below 60° C., preferably 20° to 40° C. Similar to the process A, higher temperatures may cause undesirable side reactions with acid catalysts. For instance, polymerization of the epoxide compound (IV) or cleavage of the bonds may take place. With epoxide compounds (IV) having unsaturated bonds, the isomerization of the unsaturated bonds with the acid catalyst may occur as well as the Wagner-Meerwein transfer reaction. Accordingly, the reaction temperature has to be severely controlled. The reaction proceeds in the absence of any solvent and it is most suitable to use an excess of a carbonyl compound for use also as a solvent for the reaction. However, solvents may be used in order to suppress the side reactions from occurrence and to suitably control the reaction temperature. The solvents for the reaction may be any ordinary solvents which do not give any adverse influence on the reaction. Conveniently, hydrocarbon solvents are used. Examples of the hydrocarbon solvents include aliphatic hydrocarbons such as pentane, hexane, heptane, octane and the like, aromatic hydrocarbons such as benzene, toluene, xylene and the like, alicyclic hydrocarbons such as cyclopentane, cyclohexane and the like, and mixtures thereof.

Under such reaction conditions as indicated above the dioxolan compound (VI) can be ordinarily obtained in yields over 90% and may be purified by any suitable means such as distillation.

The hydrolysis reaction of the dioxolan compound (VI) may be effected by any known procedures. It is convenient to heat the dioxolan (VI) in water using a proton-donative acid catalyst such as sulfuric acid, hydrochloric acid, phosphoric acid, benzenesulfonic acid, acetic acid or the like. The amount of the acid catalyst is not critical and is usually in the range of 0.01 to 2N, preferably 0.05 to 0.5N. Preferably, the water is admixed with water-soluble organic solvents including lower alcohols such as methanol, ethanol, isopropanol and the like, tetrahydrofuran, dioxane, and the like and the hydrolysis is effected at a temperature of 50° to 100° C. The hydrolysis of the dioxolan compound (VI) under conditions indicated above almost quantitatively gives a final product of 1,3-di-O-alkyl-2-O-2′,3′-dihydroxypropyl glycerine (I).

The final product (I) can be recovered, for example, by a method which comprises allowing the reaction mixture to stand so as to separate the product from the aqueous phase, collecting the separated product, and extracting the product dissolved in the water with a water-insoluble organic solvent.

The 1,3-di-O-alkyl-2-O-2′,3′-dihydroxypropyl glycerine has no decomposable bonds such as an ester group in the molecule thereof, so that it is very chemically stable and has surface activity only a slight degree of skin irritativeness. Thus, this product is useful as an emulsifier, oil (emolient), humectant, thickener or the like and is particularly effective as an ingredient of cosmetics.

Properties of typical 1,3-di-O-alkyl-2-O-2′,3′-dihydroxypropyl glycerine compounds are shown in Table 1 below.

TABLE 1

Physical Properties of Polyol Ether Compounds (I)

| In Formula (I) | | Form | Solubility in Water | |
|---|---|---|---|---|
| R' | R | (25° C.) | (10%)* (25° C.) | (30%)* |
| CH₃ | C₈H₁₇ | Liquid | opaque | dissolved |
| CH₃ | C₁₂H₂₅ | Liquid | formation of liquid crystal | formation of liquid crystal |
| CH₃ | C₁₄H₂₉ | Liquid | formation of liquid crystal | formation of liquid crystal |
| CH₃ | C₁₈H₃₇ | waxy | formation of liquid crystal | formation of liquid crystal |
| CH₃ | C₁₈H₃₇ (methyl-branched isostearyl) | liquid | formation of liquid crystal | formation of liquid crystal |
| C₄H₉ | C₁₈H₃₇ (methyl-branched isostearyl) | liquid | separated | separated |

*Concentrations of the product.

The 1,3-di-O-alkyl-2-O-2',3'-dihydroxypropyl glycerine products of the formula (I) in which R' represents a group having only one carbon atom are all very hydrophilic in nature, and especially the products of the formula (I) in which R represents a group having 12 to 18 carbon atoms form a liquid crystal even in an aqueous solution of low concentration. In contrast, when the number of carbon atoms of R' becomes larger, little or no solubility in water is recognized.

Although all the 1,3-di-O-alkyl-2-O-2',3'-dihydroxypropyl glycerine compounds exhibit hygroscopicity, the compounds of the formula (I) in which the number of carbon atoms of R' is one show better hygroscopicity. Of these, the compounds of the formula (I) in which R represents a hydrocarbon group having 12–18 carbon atoms are very useful as a humectant of cosmetics. Moreover, the compounds of the formula (I) in which R' represents a hydrocarbon group having only one carbon atom and R represents a hydrocarbon group having 12 to 18 carbon atoms exhibit very high emulsifying force and show excellent properties when used as an emulsifier for cosmetic emulsion.

Additionally, the compounds of the formula (I) in which R' represents a hydrocarbon group having 4 to 8 carbon atoms and R represents a hydrocarbon group having 8 or more carbon atoms have the strong tendency of being oily in nature and are thus suitable as an oil for cosmetics, serving also as an emollient which not only is hygroscopic, but also has high affinity for skin.

The amount of these compounds in cosmetics may, more or less, vary depending on various factors. When used as an emulsifier, the amount is in the range of about 0.2 to 15 wt%. Upon application as an oil or humectant, the amount is conveniently in the range of 5 to 50 wt%.

The present invention is particularly described by way of examples, which should not be construed as limiting the present invention to these examples.

REFERENCE 1

Synthesis of methyl-branched isostearyl glycidyl ether

To a 1 liter round bottom flask equipped with a reflux condenser, a dropping funnel and an agitator were added, in the following order, 120 g of an aqueous 50% sodium hydroxide solution (60 g as pure sodium hydroxide (1.5 moles), 68 g (0.25 mole) of the monomethyl-branched isostearyl alcohol obtained in Reference 2, 200 ml of n-hexane, and 25.1 g (0.0075 mole) of stearyltrimethylammonium chloride. The reaction mixture was maintained at a reaction temperature of 25° C. on a water bath, into which was dropped 93 g (1 mole) of epichlorohydrin while violently agitating at an agitation speed of 400 r.p.m. The epichlorohydrin was dropped in about 1.5 hour, after which the temperature of the reaction mixture was raised to 50° C., followed by agitating for further 8 hours at the temperature. After completion of the reaction, the reaction solution was treated as usual, thereby obtaining 68 g (yield 83%) of monomethyl-branched isostearyl glycidyl ether.

Boiling point 142°–175° C. (0.08 mmHg).

IR Spectrum (liquid film cm⁻¹): 3050, 3000, 1250, 1100, 920, 845

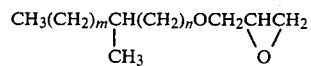

in which m is an integer of from 4 to 10, and n is an integer of from 5 to 11 provided that m+n=11 to 17 with a distribution having vertexes at m=7 and n=8.

REFERENCE 2

Synthesis of methyl-branched isostearyl alcohol

Into a 20 liters autoclave were charged 4770 g of isopropyl isostearate [Emery 2310, isopropyl isostearate, available from the Emery Co., Ltd. of U.S.A.) and 239 g of a copper-chromium catalyst (Nikki Co., Ltd.). Thereafter, hydrogen gas was charged into the autoclave at a pressure of 150 kg/cm², followed by heating the reaction mixture to 275° C. After the hydrogenation under conditions of 150 m kg/cm² and 275° C. for about 7 hours, the resulting reaction product was cooled, from which the solid catalyst was removed thereby obtaining 3500 g of a crude product. The crude product was distilled under reduced pressure to obtain 3300 g of colorless, transparent isostearyl alcohol as a distillate of 80° to 167° C./0.6 mmHg. The thus obtained isostearyl alcohol (monomethyl-branched isostearyl alcohol) had an acid value of 0.05, a saponification value of 5.5, and a hydroxyl group value of 181.4. The alcohol had absorption peaks at 3340 and 1055 cm⁻¹ in the IR analysis and at delta 3.50 (broad triplet, —CH₂—OH) in the NMR analysis (CCl₄ solvent). It was found from the gas chromatography that the alcohol was a mixture of alcohols which had about 75% of an alkyl group containing 18 carbon atoms in total with the remainder having 14 to 16 carbon atoms in total and whose branched methyl groups were positioned almost at the central portion of the alkyl main chain.

EXAMPLE 1

Synthesis of 1-O-methyl-branched isostearyl-3-O-methyl glycerine 1000 g (31.3 moles) of methanol and 11 g (0.2 mole) of MeONa were added to a 3 liters reaction vessel equipped with a reflux condenser, dropping funnel, thermometer and agitator, and were then heated. The reaction mixture was maintained at 60° C., into which 654 g (2.0 moles) of the methyl-branched isostearyl glycidyl ether obtained in Reference 1 was dropped from the dropping funnel over about 3 hours. After completion of the dropping, the reaction mixture was agitated at 60° C. for 8 hours. From the gas chromatography of the reaction mixture it was confirmed that the glycidyl ether completely disappeared. The mixture was cooled and the methanol was distilled off under reduced pressure.

By the removal of the methanol and the distillation under reduced pressure, there was obtained 650 g of a colorless, transparent liquid of 1-O-methyl-branched isostearyl-3-O-methyl glycerine.

Yield: 91%, Boiling point: 180° C.–210° C./0.7 mmHg, Elementary analysis: calculated for $C_{22}H_{46}O_3$ in parentheses, C: 73.6% (73.69%); H: 12.7% (12.93%); O: 13.4% (13.38%), Hydroxyl value: 150 (157), Average molecular weight (VPO method/HCCl$_3$): 350 (359) IR spectrum (cm$^{-1}$, liquid film): 3100–3600, 1190, 1000–1150.

NMR (CDCl$_3$, delta, TMS internal standard):

2.80 (doublet,1H, J = 3.0 Hz, C$_{18}$H$_{37}$OC$\underline{H}_2$)
  |
  CHO$\underline{H}$
  |
  CH$_3$OCH$_2$ 3.2–3.6 (multiplet, 7H, C$_{17}$H$_{35}$C$\underline{H}_2$OC$\underline{H}_2$)
  |
  $\underline{C}$HOH
  |
  CH$_3$OC$\underline{H}_2$ 3.33 (singlet, 3H, C$\underline{H}_3$O—)

EXAMPLE 2-11

The general procedure of Example 1 was repeated using various alkyl glycidyl ethers and various alcohols, thereby obtaining 1,3-di-O-alkyl glycerines. The yield and physical properties of these compounds are shown in Tables 2 and 3.

TABLE 2

1,3-Di-O—Alkyl Glycerines

ROCH$_2$\
        CHOH\
R′OCH$_2$/

| Example No. | R | R′ | Boiling Point (mm Hg) | Yield (%) | Elementary Analysis (Calcd) C (%) | H (%) | O (%) | Hydroxyl Value | Molecular Weight | Iodine Value | IR (cm$^{-1}$, liq) |
|---|---|---|---|---|---|---|---|---|---|---|---|
| 2 | n-C$_8$H$_{17}$ | CH$_3$ | 110–120° C. (1.0) | 70 | 65.9 (66.01) | 12.0 (12.00) | 22.2 (21.98) | 250 (257) | 215 (218) | — | 3100–3650 1195–970 1000–1170 |
| 3 | n-C$_{12}$H$_{25}$ | CH$_3$ | 153–155° C. (1.0) | 85 | 69.4 (70.02) | 12.5 (12.49) | 18.0 (17.49) | 200 (205) | 270 (274) | — | 3100–3650 1195, 965 1000–1170 |
| 4 | n-C$_{14}$H$_{29}$ | CH$_3$ | 170–180° C. (0.55) | 99 | 71.0 (71.47) | 12.1 (12.66) | 15.3 (15.87) | 181 (186) | — | — | 3100–3650 1200, 970 1000–1180 |
| 5 | n-C$_{16}$H$_{33}$ | CH$_3$ | 190–195° C. (0.5) | 96 | 72.8 (72.67) | 12.4 (12.81) | 14.2 (14.52) | 163 (169.7) | — | — | 3100–3650 1195, 965 1000–1180 |
| 6 | n-C$_{18}$H$_{37}$ | CH$_3$ | 41–41.8° C. (Melting Point) | 95 | 73.5 (73.69) | 12.7 (12.93) | 13.6 (13.38) | 157 (156.5) | — | — | 3100–3650 1200, 970 1000–1180 |
| 7 | C$_{18}$H$_{35}$ (Oleyl) | CH$_3$ | 189–200° C. (0.9) | 85 | 73.8 (74.10) | 12.6 (12.44) | 13.4 (13.46) | 160 (157) | 352 (357) | 68.2 (71.2) | 3100–3650 1190, 960 1000–1110 |
| 8 | C$_{18}$H$_{37}$ (Methyl-branched isostearyl) | C$_4$H$_9$ | 197–238° C. (0.4) | 80 | 74.5 (74.94) | 12.8 (13.08) | 12.5 (11.98) | 133 (140) | 401 (409) | — | 3100–3600 1000–1160 |
| 9 | C$_{18}$H$_{35}$ (Oleyl) | C$_4$H$_9$ | 210–230° C. (0.9) | 85 | 75.2 (75.32) | 12.0 (12.64) | 12.5 (12.04) | 144 (141) | 397 (399) | 62.1 (63.7) | 3100–3650 1000–1170 |
| 10 | C$_{18}$H$_{37}$ (Methyl-branched isostearyl) | C$_8$H$_{17}$ | 216–240° C. (0.3) | 80 | 76.0 (76.25) | 13.4 (13.24) | 11.0 (10.51) | 130 (123) | 450 (457) | — | 3100–3650 1000–1180 |
| 11 | C$_{18}$H$_{35}$ | C$_8$H$_{17}$ | 240–260° C. (1.0) | 85 | 76.6 (76.59) | 12.8 (12.86) | 11.0 (10.55) | 124 (123) | 450 (455) | 52.2 (55.8) | 3100–3600 1000–1170 |

TABLE 3

1,3-Di-O-Alkyl Glycerines

ROCH$_2$\
        CHOH\
ROCH$_2$/

| Example No. | R | R′ | NMR Data (CDCl$_3$, δ, TMS) OH | CHOH | Others |
|---|---|---|---|---|---|
| 2 | n-C$_8$H$_{17}$ | CH$_3$ | 2.90 (d,1H) | 3.67 (m,1H) | 3.33 (s,3H,C$\underline{H}_3$O—) 3.10~3.60 |

TABLE 3-continued 1,3-Di-O-Alkyl Glycerines $$\begin{array}{c} ROCH_2 \\ \phantom{ROCH_2}\diagdown \\ \phantom{ROCH_2}\phantom{xx}CHOH \\ \phantom{ROCH_2}\diagup \\ ROCH_2 \end{array}$$

| Example No. | R | R' | NMR Data (CDCl₃, δ, TMS) | | |
|---|---|---|---|---|---|
| | | | OH | CHOH | Others |
| 3 | n-C₁₂H₂₅ | CH₃ | 2.80 (d,1H) | 3.00 (m,1H) | 3.32 (s,3H,CH₃O—) 3.15~3.65 (m,6H,—CH₂OCH₂\CHOH/CH₃OCH₂) |
| 4 | n-C₁₄H₂₉ | CH₃ | 2.85 (d, 1H) | 3.70 (m,1H) | 3.31 (s,3H,CH₃O—) 3.10~3.60 (m,6H,—CH₂OCH₂\CHOH/CH₃OCH₂) |
| 5 | n-C₁₆H₃₃ | CH₃ | 2.83 (d,1H) | 3.68 (m,1H) | 3.30 (s,3H,CH₃O—) 3.10~3.65 (m,6H,—CH₂OCH₂\CHOH/CH₃OCH₂) |
| 6 | n-C₁₈H₃₇ | CH₃ | 2.85 (d,1H) | 3.65 (m,1H) | 3.33 (s,3H,CH₃O—) 3.05~3.60 (m,6H,—CH₂OCH₂\CHOH/CH₃OCH₂) |
| 7 | C₁₈H₃₅ (Oleyl) | CH₃ | 2.80 (d,1H) | 3.85 (m,1H) | 5.30 (t,2H,cis-Olefin) 3.33 (s,3H,CH₃O—) 3.3~3.70 (m,6H,—CH₂OCH₂\CHOH/CH₃OCH₂) |
| 8 | C₁₈H₃₇ (Methyl-branched isostearyl) | C₄H₉ | 2.75 (d,1H) | 3.73 (m,1H) | 3.20~3.70 (m,8H,—CH₂OCH₂\CHOH/CH₃OCH₂) |
| 9 | C₁₈H₃₅ (Oleyl) | C₄H₉ | 2.70 (d,1H) | 3.85 (m,1H) | 5.30 (t,2H,cis Olefin) 3.25~3.70 (m,8H,—CH₂OCH₂\CHOH/CH₃OCH₂) |

TABLE 3-continued 1,3-Di-O-Alkyl Glycerines
ROCH₂
        \
         CHOH
        /
ROCH₂

| Example No. | R | R' | NMR Data (CDCl₃, δ, TMS) | | |
|---|---|---|---|---|---|
| | | | OH | CHOH | Others |
| 10 | $C_{18}H_{37}$ (Methyl-branched isostearyl) | $C_8H_{17}$ | 2.65 (d,1H) | 3.84 (m,1H) | 3.20~3.70 (m,8H, —CH₂OCH₂\CHOH / CH₃OCH₂) |
| 11 | $C_{18}H_{35}$ (Oleyl) | $C_8H_{17}$ | 2.65 (d,1H) | 3.80 (m,1H) | 5.32 (t,2H,cis Olefin) 3.25~3.70 (m,8H, —CH₂OCH₂\CHOH / CH₃OCH₂) |

*s: singlet
d: doublet
t: triplet
m: multiplet

EXAMPLE 12

Synthesis of 1-O-methyl-branched isostearyl-3-O-methyl-2-O-2',3'-epoxypropyl glycerine (1) Into a 3 liters reaction vessel equipped with a reflux condenser, thermometer, dropping funnel and agitator were charged 416 g of an aqueous 50% sodium hydroxide solution (208 g as NaOH [5.2 moles]), 1.5 liters of hexane, and 467 g (1.3 moles) of the 1-O-methyl-branched isostearyl-3-O-methyl glycerine obtained in Example 1, followed by charging 33.1 g (0.097 mole) of tetrabutylammonium hydrogensulfate and violently agitating at 25° C. Thereafter, 301 g (3.25 moles) of epichlorohydrin was dropped portion by portion into the reaction mixture. As the dropping of the epichlorohydrin proceeded, heat was generated and the dropping was completed in about 1 hour. The reaction mixture was heated or cooled so that the temperature was maintained at 50° to 60° C. Further agitation for about 3 hours was continued to almost complete the reaction.

The reaction product was allowed to stand and the hexane phase was collected. The hexane was removed by distillation under reduced pressure and the residue was further distilled off.

As a result, there was obtained 430 g of a colorless, transparent liquid of 1-O-methyl-branched isostearyl-3-O-methyl-2-O-2',3'-epoxypropyl glycerine.

Yield: 80%, Boiling point: 195° C.-211° C./0.5 mmHg, Elementary analysis, calculated for $C_{25}H_{50}O_4$ in parentheses, C: 72.5%(72.41%), H: 12.1%(12.15%); O: 15.6%(15.43%), Average molecular weight (VPO method/HCCl₃): 410(415), Oxygen in oxirane: 3.70% (3.86%) IR spectrum (liquid film, cm⁻¹): 1240, 1000-1150, 900, 835.

NMR (delta, CCl₄, TMS internal standard): 2.33-3.90 (multiplet, 12H, RCH₂OCH₂
                                                                |
                                                          CHOCH₂CHCH₂)
                                                                |      \ /
                                                          CH₃OCH₂     O 3.28 (singlet, 3H, CH₃O—)

Synthesis of 1-O-methyl-branched isostearyl-3-O-methyl-2-O-2',3'-di-O-acetylglyceryl glycerine:

(ii) 460 g (4.5 moles) of acetic anhydride and 7.6 g (0.075 mole) of triethylamine were charged into a 2 liters reaction vessel equipped with a reflux condenser, dropping funnel, thermometer and agitator and were heated to 100° C. while agitating. Thereafter, 311 g (0.75 mole) of the glycidyl ether obtained in (i) of Example 12 was dropped from the dropping funnel. The dropping of the glycidyl ether was completed in about 1 hour. During the dropping, the reaction mixture was appropriately heated so that the reaction temperature was maintained at 100° to 120° C. The reaction mixture was continued to be agitated for about 3 hours at the temperature, so that the glycidyl ether disappeared to complete the reaction. The reaction product was cooled and subjected to distillation under reduced pressure thereby distilling off an excess of the acetic anhydride.

The resulting residue was neutralized with an aqueous diluted acid solution and extracted with ether to obtain a diester compound. The extract was distilled off under reduced pressure to obtain 380 g of a colorless, transparent liquid of 1-O-methyl-branched isostearyl-3-O-methyl-2-O-2',3'-di-O-acetylglyceryl glycerine.

Yield: 98%, Boiling point: 213° C.-240° C./0.9 mmHg, Elementary analysis: calculated for $C_{29}H_{56}O_7$ in parentheses, C: 68.1% (67.4%), H: 11.1%(10.92%), O: 20.6%(21.67%), Saponification value: 210(217), Average molecular weight: 517 (VPO/HCCl₃) (517), IR spectrum (cm⁻¹, liquid film): 1730, 1210, 1000-1150.

NMR (delta, CDCl₃, TMS internal standard)

2.0 (singlet, 6H, two acetyl groups)
3.33 (singlet, 3H, C$\underline{H}_3$O—)

3.3–3.6 (multiplet, 7H, RC$\underline{H}_2$OC$\underline{H}_2$
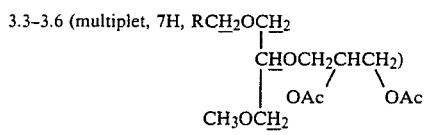

3.70 (doublet, 2H, J = 6.0 Hz, ROC$\underline{H}_2$
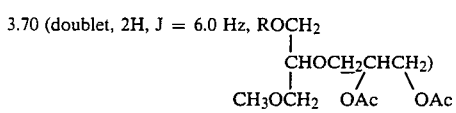

3.85–4.50 (multiplet, 2H, 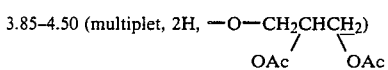

5.15 (multiplet, 1H, 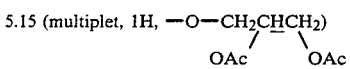

Synthesis of 1-O-methyl-branched isostearyl-3-o-methyl-2-O-2',3'-dihydroxypropyl glycerine:

(iii) 280 g of an aqueous 30% sodium hydroxide solution (84 g as NaOH (2.1 moles)) and 750 ml of ethanol were charged into a 3 liters reaction vessel equipped with a reflux condenser, dropping funnel, thermometer and agitator and agitated at room temperature. Thereafter, 359 g (0.70 mole) of the diester compound obtained in (ii) of Example 12 from the dropping funnel portion by portion. The dropping was completed in about 1 hour. The reaction mixture was heated and refluxed at 80° C. for about 3 hours. The resulting reaction product was cooled, to which were added 1 liter of water and 500 ml of ether, followed by agitating and subjecting to the phase separation. The ether phase was collected and the ether was distilled off under reduced pressure, followed by drying at 100° C./0.5 mmHg for 3 hours. As a consequence, there was obtained 298 g of a colorless, transparent liquid of 1-o-methyl-branched isostearyl-3-O-methyl-2-O-2',3'-dihydroxypropyl glycerine.

Yield: 99%, Elementary analysis: calculated for $C_{25}H_{52}O_5$ in parentheses, C: 70.0% (69.40%), H: 12.1%(12.11%), O: 18.2%(18.49%), Hydroxyl group value: 250 (259), Saponification value: 0.3 (0.0), Average molecular weight (VPO/HCCl$_3$): 430 (433), IR spectrum (cm$^{-1}$, liquid film): 3100–3550, 1190, 1000–1150.

NMR (delta, CDCl$_3$, TMS internal standard)

3.33 (singlet, 3H, C$\underline{H}_3$O—)

3.30–4.0 (multiplet, 14H, RC$\underline{H}_2$OC$\underline{H}_2$
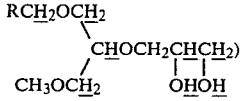

EXAMPLES 13–22

(i) According to the general procedure of Example 12(i), various 1,3-di-O-alkyl-2-O-2',3'-epoxypropyl glycerines were prepared. The yield and physical properties of these compounds are shown in Tables 4 and 5.

(ii) According to the general procedure of Example 12(ii), various 1,3-di-O-alkyl-1-O-2',3'-di-O-acetylpropyl glycerines were prepared. The yield and physical properties of these compounds are shown in Tables 6 and 7.

(iii) According to the general procedure of Example 12(iii), various 1,3-di-O-alkyl-2-O-2',3'-dihydroxypropyl glycerines were prepared. The yield and physical properties of these compounds are shown in Tables 8 and 9.

TABLE 4

1,3-Di-O—Alkyl-2-O—2',3'-Epoxypropyl Glycerines

| Example No. | R | R' | Boiling Point (mm Hg) | Yield (%) | Elementary Analysis (Calcd) | | | Other Characteristics | | |
|---|---|---|---|---|---|---|---|---|---|---|
| | | | | | C (%) | H (%) | O (%) | Oxygen in Oxirane | Molecular Weight | Iodine Value |
| 13 | n-C$_8$H$_{17}$ | CH$_3$ | 145–149° C. (0.35) | 85 | 65.5 (65.6) | 10.7 (11.02) | 23.4 (23.32) | 5.74% (5.83) | 270 (274) | — |
| 14 | n-C$_{12}$H$_{25}$ | CH$_3$ | 173–175° C. (0.3) | 86 | 68.3 (69.05) | 11.3 (11.59) | 19.4 (19.36) | 4.79 (4.84) | 327 (331) | — |
| 15 | n-C$_{14}$H$_{29}$ | CH$_3$ | 190–196° C. (0.6) | 92 | 70.0 (70.34) | 11.8 (11.81) | 18.1 (17.85) | 4.21 (4.46) | — | — |
| 16 | n-C$_{16}$H$_{33}$ | CH$_3$ | 210–215° C. (0.7) | 91 | 71.1 (71.45) | 11.8 (11.99) | 16.6 (16.55) | 3.91 (4.14) | — | — |
| 17 | n-C$_{18}$H$_{37}$ | CH$_3$ | 221–227° C. (0.7) | 84 | 72.4 (72.41) | 12.4 (12.15) | 15.2 (15.43) | 3.64 (3.86) | — | — |
| 18 | C$_{18}$H$_{35}$ (Oleyl) | CH$_3$ | 210–242° C. (0.8) | 80 | 72.7 (72.77) | 11.6 (11.72) | 15.6 (15.51) | 3.54 (3.88) | 410 (413) | 60.0 (61.5) |
| 19 | C$_{18}$H$_{37}$ (Methyl-branched Isostearyl) | C$_4$H$_9$ | 210–240° C. (0.25) | 83 | 73.1 (73.63) | 12.4 (12.36) | 14.1 (14.01) | 3.40 (3.50) | 450 (457) | — |
| 20 | C$_{18}$H$_{35}$ (Oleyl) | C$_4$H$_9$ | 235–255° C. (1.0) | 80 | 74.0 (73.96) | 11.8 (11.97) | 13.9 (14.07) | 3.28 (3.52) | 452 (455) | 54.6 (55.8) |
| 21 | C$_{18}$H$_{37}$ (Methyl-branched Isostearyl) | C$_8$H$_{17}$ | 240–260° C. (0.65) | 85 | 74.8 (74.94) | 12.6 (12.58) | 12.6 (12.45) | 3.00 (3.12) | 515 (513) | — |
| 22 | C$_{18}$H$_{35}$ (Oleyl) | C$_8$H$_{17}$ | 258–280° C. (1.0) | 81 | 75.1 (75.24) | 12.0 (12.23) | 12.9 (12.53) | 2.88 (3.13) | 510 (511) | 48.5 (49.7) |

TABLE 5

1,3-Di-O—Alkyl-2-O—2',3'-Epoxypropyl Glycerines

| Example No. | R | R' | IR(cm$^{-1}$, liq) | NMR (CDCl$_3$, δ, TMS) |
|---|---|---|---|---|
| 13 | n-C$_8$H$_{17}$ | CH$_3$ | 1195, 1000–1180, 960, 905, 840 | 2.3–3.8 (m, 12H, $-C\underline{H}_2OC\underline{H}_2$, $\underline{C}HOC\underline{H}_2CHCH_2$ (epoxide), CH$_3$OC$\underline{H}_2$); 3.30 (s, 3H, CH$_3$O—) |
| 14 | n-C$_{12}$H$_{25}$ | CH$_3$ | 1195, 1000–1080, 960, 905, 840 | 2.3–3.8 (m, 12H, same pattern); 3.25 (s, 3H, C$\underline{H}_3$O—) |
| 15 | n-C$_{14}$H$_{29}$ | CH$_3$ | 1195, 1000–1175, 960, 905, 845 | 2.3–3.8 (m, 12H, same pattern); 3.25 (s, 3H, CH$_3$O—) |
| 16 | n-C$_{16}$H$_{33}$ | CH$_3$ | 1190, 1000–1180, 960, 905, 840 | 2.3–3.8 (m, 12H, same pattern); 3.30 (s, 3H, CH$_3$O—) |
| 17 | n-C$_{18}$H$_{37}$ | CH$_3$ | 1190, 1060–1180, 960, 900, 840 | 2.3–3.8 (m, 12H, same pattern); 3.27 (s, 3H, CH$_3$O—) |
| 18 | C$_{18}$H$_{35}$ (Oleyl) | CH$_3$ | 1250, 1190, 1000–1170, 960, 905, 840 | 5.33 (t, cis-Olefin, 2H); 2.3–4.0 (m, 12H, same pattern); 3.28 (s, 3H, C$\underline{H}_3$O—) |
| 19 | C$_{18}$H$_{37}$ (Methyl-branched Iso-stearyl) | C$_4$H$_9$ | 1245, 1000–1160, 900, 835 | 2.2–3.8 (m, 14H, $-C\underline{H}_2OC\underline{H}_2$, $\underline{C}HOC\underline{H}_2CHCH_2$ (epoxide), C$_3$H$_7$C$\underline{H}_2$OC$\underline{H}_2$) |
| 20 | C$_{18}$H$_{35}$ (Oleyl) | C$_4$H$_9$ | 1250, 1000–1165, 905, 840 | 5.30 (t, cis-Olefin, 2H); 2.3–4.1 (m, 14H, same pattern as Ex. 19) |

TABLE 5-continued

1,3-Di-O—Alkyl-2-O—2',3'-Epoxypropyl Glycerines

| Example No. | R | R' | IR(cm$^{-1}$, liq) | NMR (CDCl$_3$, δ, TMS) |
|---|---|---|---|---|
| 21 | C$_{18}$H$_{37}$ (Methyl-branched Isostearyl) | C$_8$H$_{17}$ | 1255, 1000–1180, 910, 845 | 2.3–3.8 (m,14H, —C$\underline{H}_2$OC$\underline{H}_2$ / C$\underline{H}$OC$\underline{H}_2$C$\underline{H}$C$\underline{H}_2$ / C$_7$H$_{15}$C$\underline{H}_2$OC$\underline{H}_2$ O) |
| 22 | C$_{18}$H$_{35}$ (Oleyl) | C$_8$H$_{17}$ | 1250, 1000–1170, 905, 850 | 5.32(t,cis-Olefin,2H) 2.3–4.0 (m,14H, —C$\underline{H}_2$OC$\underline{H}_2$ / C$\underline{H}$OC$\underline{H}_2$C$\underline{H}$C$\underline{H}_2$ / C$_7$H$_{15}$C$\underline{H}_2$OC$\underline{H}_2$ O) |

*s: singlet
t: triplet
m: multiplet

TABLE 6

1,3-Di-O—Alkyl-2-O—2',3'-Di-O—Acetylglyceryl Glycerines:

| Example No. | R | R' | Boiling Point (mm Hg) | Yield (%) | Elementary Analysis (Calcd) C (%) | H (%) | O (%) | Saponification Value | Molecular Weight | Iodine Value | IR (cm$^{-1}$, liq) |
|---|---|---|---|---|---|---|---|---|---|---|---|
| 13 | n-C$_8$H$_{17}$ | CH$_3$ | 168–173° C. (0.8) | 95 | 60.7 (60.61) | 9.8 (9.64) | 29.6 (29.75) | 290 (298) | 360 (357) | — | 1720, 1360, 1230 1000–1180 |
| 14 | n-C$_{12}$H$_{25}$ | CH$_3$ | 192–201° C. (0.6) | 94 | 63.9 (63.86) | 10.5 (10.25) | 25.2 (25.89) | 250 (259) | 430 (425) | — | 1730, 1365, 1220 1000–1180 |
| 15 | n-C$_{14}$H$_{29}$ | CH$_3$ | 223–226° C. (0.7) | 97 | 65.5 (65.18) | 10.8 (10.50) | 24.6 (24.31) | 240 (243.6) | — | — | 1735, 1365, 1230 1000–1175 |
| 16 | n-C$_{16}$H$_{33}$ | CH$_3$ | 235–240° C. (0.7) | 98 | 66.5 (66.36) | 10.9 (10.73) | 22.4 (22.92) | 228 (230) | — | — | 1735, 1365, 1230 1000–1170 |
| 17 | n-C$_{18}$H$_{37}$ | CH$_3$ | 255–260° C. (0.8) | 96 | 67.7 (67.40) | 11.2 (10.92) | 21.5 (21.67) | 214 (217) | — | — | 1735, 1370, 1230 1000–1170 |
| 18 | C$_{18}$H$_{35}$ (Oleyl) | CH$_3$ | 235–260° C. (0.9) | 97 | 68.1 (67.67) | 10.5 (10.57) | 21.1 (21.76) | 215 (218) | 510 (515) | 50.6 (49.3) | 1730, 1360, 1220 990–1170 |
| 19 | C$_{18}$H$_{37}$ (Methyl-branched Isostearyl) | C$_4$H$_9$ | 228–260° C. (0.1) | 95 | 68.5 (68.78) | 11.1 (11.18) | 20.2 (20.04) | 195 (201) | 550 (559) | — | 1730, 1360, 1225 975–1175 |
| 20 | C$_{18}$H$_{35}$ (Oleyl) | C$_4$H$_9$ | 245–260° C. (0.7) | 95 | 69.3 (69.03) | 10.9 (10.86) | 19.7 (20.11) | 197 (202) | 550 (557) | 45.7 (45.6) | 1730, 1360, 1210 970–1170 |
| 21 | C$_{18}$H$_{37}$ (Methyl-branched isostearyl) | C$_8$H$_{17}$ | (liq) | 90 | 70.6 (70.31) | 11.5 (11.47) | 17.6 (18.21) | 180 (183) | 610 (603) | — | 1730, 1360, 1220 990–1170 |
| 22 | C$_{18}$H$_{35}$ (Oleyl) | C$_8$H$_{17}$ | (liq) | 95 | 71.3 (70.55) | 11.3 (11.18) | 17.4 (18.27) | 184 (183) | 615 (613) | 42.1 (41.4) | 1730, 1355, 1250 970–1170 |

TABLE 7

1,3-Di-O—Alkyl-2-O—2',3'-Di-O—Acetylglyceryl Glycerines

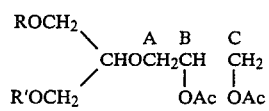

| Example No. | R | R' | —OCOCH$_3$ | H$^A$ | H$^B$ | H$^C$ | NMR Data (CDCl$_3$, δ, TMS) Others |
|---|---|---|---|---|---|---|---|
| 13 | n-C$_8$H$_{17}$ | CH$_3$ | 2.0 (s,6H) | 3.70 (d,2H) | 5.13 (m,1H) | 3.80–4.50 (m,2H) | 3.27(s,3H,CH$_3$O—) 3.20–3.80 (m,7H, —C$\underline{H}_2$OC$\underline{H}_2$ / C$\underline{H}$—O— / CH$_3$OC$\underline{H}_2$) |

TABLE 7-continued 1,3-Di-O—Alkyl-2-O—2',3'-Di-O—Acetylglyceryl Glycerines $$\begin{array}{c} ROCH_2 \\ \phantom{RO}\diagdown \\ \phantom{ROCH_2}CHOCH_2CH\phantom{-}CH_2 \\ \phantom{RO}\diagup \phantom{CHOCH_2CH}| \phantom{-}| \\ R'OCH_2 \phantom{CHOCH_2C}OAc\phantom{-}OAc \\ \phantom{ROCH_2CHOCH_2}A\phantom{-}B\phantom{-}C \end{array}$$

| Example No. | R | R' | —OCOCH$_3$ | H$^A$ | H$^B$ | H$^C$ | Others |
|---|---|---|---|---|---|---|---|
| 14 | n-C$_{12}$H$_{25}$ | CH$_3$ | 2.05 (s,6H) | 3.70 (d,2H) | 5.15 (m,1H) | 3.90–4.50 (m,2H) | 3.23(s,3H,C$\underline{H}_3$O—) 3.25–3.65 $\left(m, 7H, \begin{array}{c}-C\underline{H}_2C\underline{H}_2\\ \diagdown \\ \phantom{CH_3OCH_2}C\underline{H}O-\\ \diagup\\ CH_3OC\underline{H}_2\end{array}\right)$ |
| 15 | n-C$_{14}$H$_{29}$ | CH$_3$ | 2.05 (s,6H) | 3.71 (d,2H) | 5.14 (m,1H) | 3.90–4.50 (m,2H) | 3.25(s,3H,C$\underline{H}_2$O) 3.20–3.80 $\left(m, 7H, \begin{array}{c}R-C\underline{H}_2OC\underline{H}_2\\ \diagdown \\ \phantom{CH_3OCH_2}C\underline{H}OCH_2CHCH_2\\ \diagup\\ CH_3OC\underline{H}_2\end{array}\right)$ |
| 16 | n-C$_{16}$H$_{33}$ | CH$_3$ | 2.04 (s,6H) | 3.70 (d,2H) | 5.13 (m,1H) | 3.85–4.55 (m,2H) | 3.27(s,3H,C$\underline{H}_3$O—) 3.20–3.85 $\left(m, 7H, \begin{array}{c}R'C\underline{H}_2OC\underline{H}_2\\ \diagdown \\ \phantom{CH_3OCH_2}C\underline{H}O-\\ \diagup\\ CH_3OC\underline{H}_2\end{array}\right)$ |
| 17 | n-C$_{18}$H$_{37}$ | CH$_3$ | 2.05 (s,6H) | 3.73 (d,2H) | 5.15 (m,1H) | 3.90–4.50 (m,2H) | 3.30(s,3H, C$\underline{H}_3$O—) 3.20–3.80 $\left(m, 7H, \begin{array}{c}R'C\underline{H}_2OC\underline{H}_2\\ \diagdown \\ \phantom{CH_3OCH_2}C\underline{H}O-\\ \diagup\\ CH_3OC\underline{H}_2\end{array}\right)$ |
| 18 | C$_{18}$H$_{35}$ (Oleyl) | CH$_3$ | 2.05 (s,6H) | 3.73 (d,2H) | 5.15 (m,1H) | 3.90–4.50 (m,2H) | 3.30(s,3H,C$\underline{H}_3$O—) 3.25–3.80 $\left(m, 7H, \begin{array}{c}RC\underline{H}_2OC\underline{H}_2\\ \diagdown \\ \phantom{CH_3OCH_2}C\underline{H}O-\\ \diagup\\ CH_3OC\underline{H}_2\end{array}\right)$ 5.33(t,2H,cis olefin) |
| 19 | C$_{18}$H$_{37}$ (Methyl-branched Isostearyl) | C$_4$H$_9$ | 2.07 (s,6H) | 3.73 (d,2H) | 5.15 (m,1H) | 3.93–4.55 (m,2H) | 3.25–3.70 $\left(m, 9H, \begin{array}{c}-C\underline{H}_2OC\underline{H}_2\\ \diagdown \\ \phantom{C_3H_7CH_2OCH_2}C\underline{H}O-\\ \diagup\\ O_3H_7-C\underline{H}_2OC\underline{H}_2\end{array}\right)$ |
| 20 | C$_{18}$H$_{35}$ (Oleyl) | C$_4$H$_9$ | 2.03 (s,6H) | 3.73 (d,2H) | 5.13 (m,1H) | 3.85–4.50 (m,2H) | 3.20–3.80 $\left(m, 9H, \begin{array}{c}-C\underline{H}_2OC\underline{H}_2\\ \diagdown \\ \phantom{C_3H_7CH_2OCH_2}C\underline{H}O-\\ \diagup\\ C_3H_7C\underline{H}_2OC\underline{H}_2\end{array}\right)$ 5.33 (t,2H,cis olefin) |
| 21 | C$_{18}$H$_{37}$ (Methyl-branched Isostearyl) | C$_8$H$_{17}$ | 2.05 (s,6H) | 3.73 (d,2H) | 5.15 (m,1H) | 3.92–4.55 (m,2H) | 3.20–3.70 $\left(m, 9H, \begin{array}{c}-C\underline{H}_2OC\underline{H}_2\\ \diagdown \\ \phantom{C_7H_{15}CH_2OCH_2}C\underline{H}O-\\ \diagup\\ C_7H_{15}-C\underline{H}_2OC\underline{H}_2\end{array}\right)$ |

TABLE 7-continued 1,3-Di-O—Alkyl-2-O—2',3'-Di-O—Acetylglyceryl Glycerines

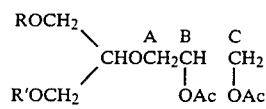

| Example No. | R | R' | NMR Data (CDCl₃, δ, TMS) | | | | |
|---|---|---|---|---|---|---|---|
| | | | —OCOCH₃ | $H^A$ | $H^B$ | $H^C$ | Others |
| 22 | C₁₈H₃₅ (Oleyl) | C₈H₁₇ | 2.05 (s,6H) | 3.75 (d,2H) | 5.13 (m,1H) | 3.90–4.55 (m,2H) | 3.20–3.70 (m,9H, —C$\underline{H}$₂OC$\underline{H}$₂\ /C$\underline{H}$O— C₇H₁₅—C$\underline{H}$₂OC$\underline{H}$₂) 5.32(t,2H,cis olefin) |

TABLE 8

1,3-Di-O—Alkyl-2-O—2',3'-Dihydroxypropyl Glycerines

| Example No. | R | R' | Yield (%) | Elementary Analysis (Calcd) C (%) | H (%) | O (%) | Other Characteristics (Calcd) Hydroxyl Group | Iodine Value | IR (cm⁻¹, liq) |
|---|---|---|---|---|---|---|---|---|---|
| 13 | n-C₈H₁₇ | CH₃ | 97 (liq) | 61.5 (61.61) | 11.1 (11.03) | 26.7 (27.36) | 380 (384) | — | 3000–3600 1190 990–1170 |
| 14 | n-C₁₂H₂₅ | CH₃ | 98 (liq) | 65.2 (65.48) | 11.5 (11.57) | 22.5 (22.95) | 320 (322) | — | 3000–3600 1180 990–1160 |
| 15 | n-C₁₄H₂₉ | CH₃ | 98 (liq) | 66.8 (66.98) | 12.1 (11.78) | 21.4 (21.24) | 288 (298) | — | 3100–3650 1195 1000–1180 |
| 16 | n-C₁₆H₃₃ | CH₃ | 98 mp 33–33.5° C. | 68.1 (68.27) | 12.3 (11.96) | 19.6 (19.77) | 275 (277) | — | 3100–3650 1200 1000–1180 |
| 17 | n-C₁₈H₃₇ | CH₃ | 99 mp 44–45° C. | 69.4 (69.40) | 12.5 (12.11) | 18.1 (18.49) | 260 (259) | — | 3100–3650 1200 1000–1180 |
| 18 | C₁₈H₃₅ (Oleyl) | CH₃ | 97 (liq) | 69.8 (69.72) | 11.9 (11.70) | 18.3 (18.57) | 260 (261) | 59.2 (58.9) | 3100–3600 1190 990–1170 |
| 19 | C₁₈H₃₇ (Methyl-branched Isostearyl) | C₄H₉ | 95 (liq) | 71.1 (70.84) | 12.4 (12.31) | 16.6 (16.35) | 230 (236) | — | 3100–3600 1000–1170 |
| 20 | C₁₈H₃₅ (Oleyl) | C₄H₉ | 98 (liq) | 71.0 (71.14) | 12.1 (11 ) | 16.9 (16.92) | 235 (237) | 53.6 (53.7) | 3100–3600 990–1170 |
| 21 | C₁₈H₃₇ (Methyl-branched Isostearyl) | C₈H₁₇ | 97 (liq) | 72.8 (72.40) | 12.6 (12.53) | 14.9 (15.07) | 205 (211) | — | 3100–3600 960–1160 |
| 22 | C₁₈H₃₅ (Oleyl) | C₈H₁₇ | 97 (liq) | 73.1 (72.68) | 12.4 (12.20) | 14.8 (15.13) | 210 (212) | 49.4 (48.0) | 3100–3600 1000–1160 |

TABLE 9

1,3-Di-O—Alkyl-2-O—2',3'-Dihydroxypropyl Glycerines

| Example No. | R | R' | NMR Data (CDCl₃, δ, TMS) |
|---|---|---|---|
| 13 | n-C₈H₁₇ | CH₃ | 3.38(s,3H,C$\underline{H}$₃O—) 3.0–4.0 (m,14H, —C$\underline{H}$₂OC$\underline{H}$₂\ /CHOCH₂C$\underline{H}$C$\underline{H}$₂ CH₃OC$\underline{H}$₂ O$\underline{H}$O$\underline{H}$) |
| 14 | n-C₁₂H₂₅ | CH₃ | 3.35(s,3H,C$\underline{H}$₃O—) 3.1–4.0 (m,14H, —C$\underline{H}$₂OC$\underline{H}$₂\ /CHOCH₂C$\underline{H}$C$\underline{H}$₂ CH₃OC$\underline{H}$₂ O$\underline{H}$O$\underline{H}$) |

TABLE 9-continued

1,3-Di-O—Alkyl-2-O—2',3'-Dihydroxypropyl Glycerines

| Example No. | R | R' | NMR Data (CDCl$_3$, δ, TMS) |
|---|---|---|---|
| 15 | n-C$_{14}$H$_{29}$ | CH$_3$ | 3.35(s,3H,C$\underline{H}_3$O—)<br>3.10–4.05<br>$\left( m,14H, \begin{array}{c} -C\underline{H}_2OC\underline{H}_2 \\ CH_3OC\underline{H}_2 \end{array} \Big\rangle C\underline{H}OC\underline{H}_3C\underline{H}C\underline{H}_2 \atop \quad\quad O\underline{H}O\underline{H} \right)$ |
| 16 | n-C$_{16}$H$_{33}$ | CH$_3$ | 3.35(s,3H,C$\underline{H}_3$O—)<br>3.10–4.05<br>$\left( m,14H, \begin{array}{c} -C\underline{H}_2OC\underline{H}_2 \\ CH_3OC\underline{H}_2 \end{array} \Big\rangle C\underline{H}OC\underline{H}_2C\underline{H}C\underline{H}_2 \atop \quad\quad O\underline{H}O\underline{H} \right)$ |
| 17 | n-C$_{18}$H$_{37}$ | CH$_3$ | 3.30(s,3H,C$\underline{H}_3$O—)<br>3.10–4.05<br>$\left( m,14H, \begin{array}{c} -C\underline{H}_2OC\underline{H}_2 \\ CH_3OC\underline{H}_2 \end{array} \Big\rangle C\underline{H}OC\underline{H}_2C\underline{H}C\underline{H}_2 \atop \quad\quad O\underline{H}O\underline{H} \right)$ |
| 18 | C$_{18}$H$_{35}$<br>(Oleyl) | CH$_3$ | 3.35(s,3H,C$\underline{H}_3$O—)<br>3.3–4.15<br>$\left( m,14H, \begin{array}{c} -C\underline{H}_2OC\underline{H}_2 \\ CH_3OC\underline{H}_2 \end{array} \Big\rangle C\underline{H}OC\underline{H}_2C\underline{H}C\underline{H}_2 \atop \quad\quad O\underline{H}O\underline{H} \right)$<br>5.33(t,2H,Olefin Proton) |
| 19 | C$_{18}$H$_{37}$<br>(Methyl-branched Isostearyl) | C$_4$H$_9$ | 3.1–4.0<br>$\left( m,16H, \begin{array}{c} -C\underline{H}_2OC\underline{H}_2 \\ C_3H_7-C\underline{H}_2OC\underline{H}_2 \end{array} \Big\rangle C\underline{H}OC\underline{H}_2C\underline{H}C\underline{H}_2 \atop \quad\quad O\underline{H}O\underline{H} \right)$ |
| 20 | C$_{18}$H$_{35}$<br>(Oleyl) | C$_4$H$_9$ | 3.25–4.05<br>$\left( m,16H, \begin{array}{c} -C\underline{H}_2OC\underline{H}_2 \\ C_3H_7-C\underline{H}_2OC\underline{H}_2 \end{array} \Big\rangle C\underline{H}OC\underline{H}_2C\underline{H}C\underline{H}_2 \atop \quad\quad O\underline{H}O\underline{H} \right)$<br>5.34(t,2H,Olefin Proton) |
| 21 | C$_{18}$H$_{37}$<br>(Methyl-branched Isostearyl) | C$_8$H$_{17}$ | 3.15–4.0<br>$\left( m,16H, \begin{array}{c} -C\underline{H}_2OC\underline{H}_2 \\ C_7H_{15}-C\underline{H}_2OC\underline{H}_2 \end{array} \Big\rangle C\underline{H}-O-C\underline{H}_2-C\underline{H}C\underline{H}_2 \atop \quad\quad\quad\quad O\underline{H}O\underline{H} \right)$ |
| 22 | C$_{18}$H$_{35}$<br>(Oleyl) | C$_8$H$_{17}$ | 3.25–4.10<br>$\left( m,16H, \begin{array}{c} -C\underline{H}_2OC\underline{H}_2 \\ C_7H_{15}-C\underline{H}_2OC\underline{H}_2 \end{array} \Big\rangle C\underline{H}OC\underline{H}_2-C\underline{H}C\underline{H}_2 \atop \quad\quad\quad O\underline{H}O\underline{H} \right)$<br>5.33(t,2H,Olefin Proton) |

*s: singlet;
m: multiplet;
t: triplet

EXAMPLE 23

Synthesis of 1-O-methyl-branched isostearyl-3-O-methyl-2-O-2',3'-O-isopropylideneglyceryl glycerine (i) 319 g (5.5 moles) of acetone and 4 g (0.028 mole) of boron trifluoride etherate were charged into a 3 liters reaction vessel equipped with a reflux condenser, dropping funnel, thermometer and agitator and agitated at 25° C. Thereafter, 228 g (0.51 mole) of the glycidyl ether obtained in Example 12(i) was added portion by portion from the dropping funnel. By the dropping of the glycidyl ether, the reaction mixture gradually generated heat of reaction. The mixture was allowed to stand at room temperature without cooling. The dropping of the glycidyl ether was completed in about 2 hours. After further agitation for 30 minutes, it was confirmed from the gas chromatograph of the reaction mixture that the glycidyl ether disappeared. The reaction product was admixed with 11.8 g (0.14 mole) of sodium bicarbonate and heated to distil off the acetone. After completion of the distillation of the acetone, a mixture of water (500 ml)/ether (1 liter) was added to the reaction mixture, followed by extraction with ether while agitation. The ether phase was collected by the phase separation. After removal of the ether by distillation under reduced pressure, the residue was distilled under reduced pressure. As a result, there was obtained 221 g of a colorless, transparent liquid of 1-O-methyl-branched isostearyl-3-o-methyl-2-O-2',3'-O-isopropylideneglyceryl glycerine.

Yield: 85%, Boiling point: 220° C.–248° C./0.7 mmHg, Elementary analysis: calculated for $C_{28}H_{56}O_5$ in parentheses, C: 70.7%(71.14%), H: 11.9%(11.94%), O: 17.3%(16.92%), Average molecular weight (VPO method/$HCCl_3$): 465(473), IR spectrum (cm$^{-1}$, liquid film): 1380, 1370, 1255, 1210, 1000–1170, 840.

NMR (delta, $CCl_4$, TMS):

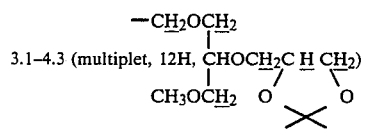

3.1–4.3 (multiplet, 12H, $CHOCH_2C\underline{H}CH_2$)

3.20 (singlet, 3H, $C\underline{H}_3O$—)

Isopropylidene proton

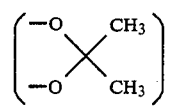

is found to be superposed on the methylene proton region.

Synthesis of 1-O-methyl-branched isostearyl-3-O-methyl-2-o-2',3'-dihydroxypropyl glycerine (ii) 103 g (0.22 mole) of the dioxolan compound obtained in Example 23(i), 250 ml of methanol and 250 ml of water were charged into a 1 liter reaction vessel equipped with a reflux condenser, thermometer and agitator and were violently agitated. Thereafter, 12.3 g (0.126 mole) of concentrated sulfuric acid was added, followed by heating under reflux. After the refluxing over about 4 hours, it was confirmed from the IR spectra of the reaction mixture that the hydrolysis was completed. The reaction product was cooled and the organic phase was collected by phase separation. The aqueous phase was subjected to extraction with ether (500 ml). The ether phase was collected by phase separation and combined with the previously obtained organic phase, to which an aqueous sodium bicarbonate solution was added for neutralization of the acid components therewith. Subsequently, the ether phase was collected by phase separation. The ether was removed by distillation under reduced pressure, after which the residue was heated and dried under conditions of 100° C./0.5 mmHg for about 3 hours. As a result, there was obtained 93 g of a colorless, transparent liquid of 1-O-methyl-branched isostearyl-3-O-methyl-2-O-2',3'-dihydroxypropyl glycerine.

Yield: 98.6%, Elementary analysis: calculated for $C_{25}H_{52}O_5$ in parentheses, C: 70.0%(69.40%), H: 12.1%(12.11%), O: 18.2%(18.49%), Hydroxyl group value: 250(259), Average molecular weight: 430 (433), IR spectrum (cm$^{-1}$, liquid film): 3100–3550, 1190, 1000–1150.

NMR ($CDCl_3$, delta, TMS):

3.33 (singlet, 3H, $C\underline{H}_3O$—)

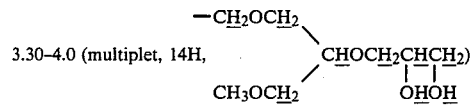

3.30–4.0 (multiplet, 14H, ...)

EXAMPLES 24–30

(i) According to the general procedure of Example 23(i), various 1,3-di-O-alkyl-2-O-2',3'-O-isopropylideneglyceryl glycerines were prepared. The yield and physical properties of these compounds are shown in Tables 10 and 11.

(ii) According to the general procedure of Example 23(ii), various 1,3-di-O-alkyl-2-O-2',3'-dihydroxypropyl glycerines were prepared. These compounds were quantitatively obtained and had the same physical values as those obtained in (iii) of Examples 13, 14, 18–22, respectively.

TABLE 10

1,3-Di-O—Alkyl-2-O—2',3'-O—Isopropylideneglyceryl Glycerine

| Example No. | R | R' | Boiling Point (mm Hg) | Yield % | Elementary Analysis (Calcd) C % | H % | O % | Molecular Weight (VPO/HCCl$_3$) | IR (liq. cm$^{-1}$) |
|---|---|---|---|---|---|---|---|---|---|
| 24 | n-C$_8$H$_{17}$ | CH$_3$ | 165–170° C. (2.0) | 85 | 64.8 (65.03) | 10.6 (10.91) | 24.1 (24.06) | 330 (333) | 1380, 1370, 1250, 1210. 1000–1180, 840 |
| 25 | n-C$_{12}$H$_{25}$ | CH$_3$ | 178–180° C. (0.6) | 87 | 67.6 (68.00) | 11.6 (11.41) | 20.9 (20.59) | 390 (389) | 1380, 1370, 1260, 1220, 1000–1180, 845 |
| 26 | C$_{18}$H$_{35}$ (Oleyl) | CH$_3$ | 224–265° C. (0.7) | 82 | 71.5 (71.44) | 11.8 (11.56) | 17.2 (16.99) | 415 (471) | 1380, 1370, 1250, 1200, 980–1170, 830 |

TABLE 10-continued

| | 1,3-Di-O—Alkyl-2-O—2',3'-O—Isopropylideneglyceryl Glycerine | | | | | | | | |
|---|---|---|---|---|---|---|---|---|---|
| Example No. | R | R' | Boiling Point (mm Hg) | Yield % | Elementary Analysis (Calcd) | | | Molecular Weight (VPO/HCCl₃) | IR (liq. cm⁻¹) |
| | | | | | C % | H % | O % | | |
| 27 | C₁₈H₃₇ (Methyl-branched Isostearyl) | C₄H₉ | 220–250° C. (0.5) | 85 | 71.9 (72.32) | 12.2 (12.14) | 15.2 (15.54) | 510 (515) | 1380, 1370, 1245, 1200, 1000–1180, 840 |
| 28 | C₁₈H₃₅ (Oleyl) | C₄H₉ | 235–270° C. (0.4) | 81 | 72.0 (72.61) | 11.5 (11.79) | 15.5 (15.60) | 520 (513) | 1380, 1370, 1250, 1205, 990–1180, 845 |
| 29 | C₁₈H₃₇ (Methyl-branched Isostearyl) | C₈H₁₇ | 235–275° C. (0.4) | 83 | 73.4 (73.63) | 12.0 (12.36) | 13.5 (14.01) | 565 (571) | 1380, 1365, 1250, 1200, 1000–1175, 845 |
| 30 | C₁₈H₃₅ (Oleyl) | C₈H₁₇ | liquid | 80 | 74.0 (73.89) | 12.3 (12.05) | 14.1 (14.06) | 560 (569) | 1380, 1370, 1255, 1210, 1000–1180, 840 |

TABLE 11

| | 1,3-Di-O—Alkyl-2-O—2',3'-O—Isopropylideneglyceryl Glycerine | | | |
|---|---|---|---|---|
| | | | NMR Data (CDCl₃, δ, TMS)* | |
| Example No. | R | R' | Isopropylidene $\begin{array}{c}-O\\-O\end{array}\!\!\!\!\diagdown\!\!\!\!\diagup\begin{array}{c}CH_3\\CH_3\end{array}$ | Others |
| 24 | n-C₈H₁₇ | CH₃ | 1.34(s,3H) 1.38(s,3H) | 3.37(s,3H,C$\underline{H}$₃O—) 3.3–4.5 {m,12H, —C$\underline{H}$₂OC$\underline{H}$₂, CH₃OC$\underline{H}$₂ / CHOC$\underline{H}$₂CHCH₂ with O O joined by X} |
| 25 | n-C₁₂H₂₅ | CH₃ | Superposed on the Methylene Proton (—CH₂) | 3.30(s,3H,C$\underline{H}$₃O—) 3.3–4.4 {m,12H, —C$\underline{H}$₂OC$\underline{H}$₂, CH₃OC$\underline{H}$₂ / CHOC$\underline{H}$₂CHCH₂ with O O joined by X} |
| 26 | C₁₈H₃₅ (Oleyl) | CH₃ | Superposed on the Methylene Proton (—CH₂) | 3.34(s,3H,C$\underline{H}$₃O—) 3.30–4.4 {m,12H, —C$\underline{H}$₂OC$\underline{H}$₂, CH₃OC$\underline{H}$₂ / CHOC$\underline{H}$₂CHCH₂ with O O joined by X} 5.32(t,2H,Olefin Proton) |
| 27 | C₁₈H₃₇ (Methyl-branched Isostearyl) | C₄H₉ | Superposed on the Methylene Proton (—CH₂) | 3.2–4.4 {m,14H, —C$\underline{H}$₂OC$\underline{H}$₂, C₃H₇C$\underline{H}$₂OC$\underline{H}$₂ / CHOC$\underline{H}$₂CHCH₂ with O O joined by X} |
| 28 | C₁₈H₃₅ (Oleyl) | C₄H₉ | Superposed on the Methylene Proton (—CH₂) | 5.33(t,2H,Olefin Proton) 3.25–4.40 {m,14H, —C$\underline{H}$₂OC$\underline{H}$₂, C₃H₇C$\underline{H}$₂OC$\underline{H}$₂ / CHOC$\underline{H}$₂CHCH₂ with O O joined by X} |

TABLE 11-continued 1,3-Di-O—Alkyl-2-O—2',3'-O—Isopropylideneglyceryl Glycerine

NMR Data (CDCl₃, δ, TMS)*

| Example No. | R | R' | Isopropylidene −O\CH₃ / −O/ \CH₃ | Others |
|---|---|---|---|---|
| 29 | C₁₈H₃₇ (Methyl-branched Isostearyl) | C₈H₁₇ | Superposed on the Methylene Proton (—CH₂) | 3.2–4.4 (m,14H, —CH₂OCH₂\ /CHOCH₂CHCH₂ C₇H₁₅CH₂OCH₂ / \|   \| O   O \X/) |
| 30 | C₁₈H₃₅ (Oleyl) | C₈H₁₇ | Superposed on the Methylene Proton (—CH₂) | 5.30(t,2H,Olefin Protons) 3.20–4.40 (m,14H, —CH₂OCH₂\ /CHOCH₂CHCH₂ C₇H₁₅CH₂OCH₂ / \|   \| O   O \X/) |

*s: singlet;
t: triplet;
m: multiplet

EXAMPLE 31

1,3-di-O-alkyl-2-O-2',3'-dihydroxypropyl glycerines were subjected to the test of hygroscopicity and were compared with one another to determine their properties as a humidity retainer.

The hygroscopic test was effected as follows: a given amount of each compound to be tested which had been preliminarily dried was kept under constant temperature and humidity conditions of a humidity of 93% and a temperature of 25° C. and an increasing rate of the weight was checked. The results are shown in Table 12 below.

TABLE 12

| Tested Compounds of Formula (I) | | Hygroscopicity* | |
|---|---|---|---|
| R' | R | After One Day | After 14 Days |
| CH₃ | n-C₈H₁₇ | 13 | 23 |
| CH₃ | n-C₁₄H₂₉ | 9 | 20 |
| CH₃ | n-C₁₈H₃₇ | 8 | 15 |
| CH₃ | C₁₈H₃₇ (methyl-branched isostearyl) | 7 | 13 |
| C₄H₉ | C₁₈H₃₇ (methyl-branched isostearyl) | 6 | 7 |

*Hygroscopicity = $\frac{\text{Weight of absorbed compound (g)} - \text{Dry weight of tested compound (g)}}{\text{Dry weight of tested compound (g)}} \times 100$ As will be apparent from the above results, all the tested compounds of the present invention exhibit a certain degree of hygroscopicity and the compounds of the formula (I) in which R' represents a group having one carbon atom and particularly R represents a group having 8 to 14 carbon atoms show high hygroscicipity, thus begin excellent as a humidity retainer.

EXAMPLE 32

1,3-di-O-dialkyl-2-O-2',3'-dihydroxypropyl glycerines were used for an emulsification test to compare emulsifying forces with one another.

The emulsification test was effected using liquid paraffin under the following conditions. 20 part of liquid paraffin was admixed with 2 part of a compound to be tested and heated to 75° C. Separately, 78 parts of purified water was heated to 75° C. and was added for emulsification to the mixture of the liquid paraffin and the compound being tested. After the emulsification, the mixture was cooled to room temperature while agitating.

The emulsifying ability was evaluated as follows: the state of the emulsion immediately after the production and the separated state after storage at 25° C. for 7 days were observed. The results are shown in Table 13.

TABLE 13

| Tested Compounds of Formula (I) | | State Immediately After Formation | Separation Rate After 7 Days* |
|---|---|---|---|
| R' | R | | |
| Product of Invention | | | |
| CH₃ | n-C₈H₁₇ | Separated into oil and water | 100 |
| CH₃ | n-C₁₂H₂₅ | Homogeneous o/w cream | 0 |
| CH₃ | n-C₁₄H₂₉ | Separated into oil and water | 100 |
| CH₃ | n-C₁₈H₃₇ | Inhomogeneous w/o cream | 23 |
| CH₃ | i-C₁₈G₃₇ (methyl-branced isostearyl) | Homogeneous w/o cream | 3 |
| C₄H₉ | n-C₁₈H₃₇ | Separated into oil and water | 100 |
| C₈H₁₇ | n-C₁₈H₃₇ | Separated into oil and water | 100 |
| Comparative Products | | | |
| Glycerol monostearate | | Slightly inhomogeneous w/o cream | 56 |
| Glycerol monooleate | | Homogeneous w/o cream | 5 |
| Sorbitan monooleate | | Slightly inhomogeneous w/o cream | 8 |

*Separation Rate = $\frac{\text{Amount of separated oil phase (ml)} + \text{Amount of separated water phase (ml)}}{\text{Total amount (ml)}} \times 100$ As will become apparent from the above results, the compounds of the present invention of the formula (I) in which R' has only one carbon atom and R has 12 carbon atoms and in which R has 18 carbon atoms show, as o/w and w/o emulsions, respectively, an emulsifying stability equal to or higher than known glycerol esters or sorbitan esters which are believed to have a high emulsifying force.

EXAMPLE 33

Lotions 1,3-Di-O-alkyl-2-O-2',3'-dihydroxypropyl glycerine was used as a humidity retainer and a lotion of the following composition was prepared.

| | |
|---|---|
| 1-O—octyl-3-O—methl-2-O—2'.3'-dihydroxypropyl glycerine | 5.0 (wt %) |
| Glycine | 1.0 |
| Sodium pyrrolidonecarboxylate | 1.0 |
| Ethanol | 15.0 |
| Polyoxxyethylene cetyl ether | 1.5 |
| Perfume | 0.2 |
| Purified water | Balance |

The lotion containing the compound of the present invention was not sticky and was soft to the touch.

EXAMPLE 34

W/O Cream 1,3-Di-O-alkyl-2-O-2',3'-dihydroxypropyl glycerine was used as an emulsifier so as to prepare an emulsion of the following composition.

| | | |
|---|---|---|
| A | Liquid paraffin | 14.0 (wt %) |
| | Squalane | 14.0 |
| | 1-O—isostearyl-3-O—methyl-2-O—2',3'-dihydroxypropyl glycerine | 2.0 |
| B | Propylene glycol | 4.0 |
| | Sodium benzoate | 0.2 |
| | Purified water | Balance |

The ingredients of A were mixed and heated to 75° C. To the mixture was gradually added a mixture of ingredients B, which had been previously mixed and heated, under agitation for emulsification. Thereafter, the mixture was cooled to room temperature while agitating, thereby obtaining and emulsion. The thus obtained emulsion was a w/o-type cream with good emulsifying stability and was so good to the touch that it was considered suitable as a cosmetic cream.

EXAMPLE 35

1,3-Di-O-alkyl-2-O-2',3'-dihydroxypropyl glycerine was used as an oil so as to prepare a mixture of the following composition.

| | | |
|---|---|---|
| A | Liquid paraffin | 25.0 (wt %) |
| | Isopropyl palmitate | 15.0 |
| | 1-O—isostearyl-3-O—octyl-2-O—dihydroxypropyl glycerine | 12.0 |
| | Microcrystalline wax | 7.0 |
| | Candelilla wax | 1.0 |
| B | Titanium oxide | 15.0 |
| | Kaoline | 15.0 |
| | Talc | 6.0 |
| | Coloring pigment | 4.0 |

Ingredients A were mixed, heated and molten homogeneously. Ingredients B which had been previously mixed were added to the ingredients A, followed by kneading the mixture on a roll mill. The kneaded mixture was remolten and poured into a container for shaping.

The resulting mixture was a solt solid and had an excellent affinity for skin when used as an oily foundation.

What is claimed is:

1. A polyol ether compound represented by the general formula (I):

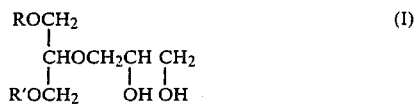

in which R represents a saturated or unsaturated, straight-chain or branched aliphatic hydrocarbon group having 8 to 24 carbon atoms, and R' represents a saturated or unsaturated, straight-chain or branched hydrocarbon group having 1 to 24 carbon atoms.

2. A polyol ether compound according to claim 1, wherein R' represents a lower alkyl group having 1 to 3 carbon atoms, and R represents a saturated or unsaturated, straight-chain or branched aliphatic hydrocarbon group having 8 to 20 carbon atoms.

3. A polyol ether compound according to claim 2, wherein R represents a octyl group.

4. A polyol ether compound according to claim 2, wherein R represents a dodecyl group.

5. A polyol ether compound according to claim 2, wherein R represents a methyl-branched isostearyl group represented by the following formula:

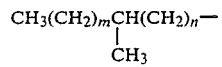

in which m is an integer of from 4 to 10, and n is an integer of from 5 to 11 provided that m+n is an integer of from 11 to 17 with a distribution having vertexes at m=7 and n=8.

6. A polyol ether compound according to claim 5, wherein R' represents a methyl group.

7. A polyol ether compound according to claim 2, wherein R represents an oleyl group.

8. A polyol ether compound according to claim 7, wherein R' represents a methyl group.

9. A polyol ether compound according to claim 1, wherein R represents a methyl-branched isostearyl group represented by the following formula:

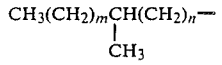

in which m is an integer of from 4 to 10, and n is an integer of from 5 to 11 provided that m+n is an integer of from 11 to 17 with a distribution having vertexes at m=7 and n=8, and R' represents a saturated or unsaturated, straight-chain or branched hydrocarbon group having 4 to 18 carbon atoms.

10. A polyol ether compound according to claim 9, wherein R' represents a butyl group.

11. A polyol ether compound according to claim 9, wherein R' represents an octyl group.

12. A polyol ether compound according to claim 1, wherein R represents an oleyl group, and R' represents a saturated or unsaturated, straight-chain or branched hydrocarbon group having 4 to 18 carbon atoms.

13. A polyol ether compound according to claim 12, wherein R' represents a butyl group.

14. A polyol ether compound according to claim 12, wherein R' represents an octyl group.

15. A cosmetic cream, emulsion or lotion which comprises the polyol ether compound of claim 1 as an emulsifier in combination with oil and water.

* * * * *